US00PP31258P3

(12) United States Plant Patent
Knott

(10) Patent No.: US PP31,258 P3
(45) Date of Patent: Dec. 24, 2019

(54) ORANGE TREE NAMED 'RED LINA'

(50) Latin Name: *Citrus sinensis*
Varietal Denomination: Red Lina

(71) Applicant: Glenam Knott, Fort Beayfort (ZA)

(72) Inventor: Glenam Knott, Fort Beayfort (ZA)

( * ) Notice: Subject to any disclaimer, the term of this patent is extended or adjusted under 35 U.S.C. 154(b) by 0 days.

(21) Appl. No.: 15/932,522

(22) Filed: Mar. 9, 2018

(65) Prior Publication Data

US 2019/0281742 P1 Sep. 12, 2019

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202, 201
CPC ..... A01H 5/08; A01H 5/0806; A01H 6/78; A01H 6/784; A01H 6/785
See application file for complete search history.

(56) References Cited

PUBLICATIONS

CGACC Newsletter 2017, retrieved on Apr. 16, 2019, retrieved from the Internet at http://www.cgacc.co.za/images/Archives/CGACC_E-mail_newsletter_December_2017_stdres.pdf, 2 pp. (Year: 2017).*
Citrus Growers' Association of Southern Africa Annual Report 2017, retrieved on Apr. 16, 2019, retrieved from the Internet at https://c1e39d912d21c91dce811d6da9929ae8.cdn.ilink247.com/ClientFiles/cga/CitrusGowersAssociation/Company/Documents/CGA%20AR%202017%20%20Final.pdf, pp. 1-2, 44. (Year: 2016).*
Upov Pluto Plant Variety Database Apr. 11, 2019, retrieved on Apr. 16, 2019, retrieved from the Internet at https://www.upov.int/pluto/en/index.jsp, 3 pp. (Year: 2019).*

* cited by examiner

*Primary Examiner* — June Hwu
(74) *Attorney, Agent, or Firm* — Cassandra Bright

(57) ABSTRACT

A new and distinct navel orange distinguished by production of fruit that combines early season maturity and a dark orange to red pigmented rind, (UPOV Group 20), with a pink albedo. It further distinguishes itself with a deep orange red flesh, and early season harvest maturity. Both flesh and juice are consistently darker than commercially known varieties. The new cultivar is a *Citrus sinensis*, useful for commercial fruit production.

10 Drawing Sheets

Latin name of the genus and species: *Citrus sinensis*.

BACKGROUND OF THE INVENTION

The new variety 'Red Lina' originated as a spontaneous branch mutation discovered by Glenam Knott in an orchard of *Citrus sinensis* 'Lina'. The discovery was made during 2009 in Eastern Cape, South Africa. On 3rd Oct. 2009, plant material was selected from the mutation branch for clean up at the *Citrus* Research International in Nelspruit. This is an extended and confidential process. In addition to the clean-stock production, in February 2010 the inventor began assessing the new variety confidentially at his own orchard in Eastern Cape, South Africa. Buds from the mutation branch were top grafted onto 'Swingle' rootstock with 'Cara Cara' Navel interstock in February 2010. The interstock was employed to improve compatibility due to 'Lina' navel's slight incompatibility with 'Swingle' rootstock. Fruit production on these trees commenced on 2013. Additional propagation of 'Red Lina' direct onto Swingle rootstock were made at the same site to replace failed top grafts in 2013.

Various instabilities, including foliar variegation were observed. After 6 generations a final selection was made of a stable clone.

SUMMARY OF THE INVENTION

The cultivar 'Red Lina' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Red Lina'. These characteristics in combination distinguish 'Red Lina' as a new and distinct *Citrus sinensis* cultivar:

1. Early season maturity.
2. Dark orange pigmented rind, occasionally with red blush.
3. Red pigmented flesh.
4. Red pigmented albedo.
5. Round, small fruit shape, less oblong.
6. Higher percentage of the fruit have a less protruding navel end.

COMPARISON TO PARENT VARIETY

Plants of the new cultivar 'Red Lina' are similar to plants of the seed parent, *Citrus sinensis* 'Lina' in most horticultural characteristics, however, plants of the new cultivar 'Red Lina' differs in the following ways;

1. New cultivar's growth shape is more spherical and more compact than parent variety.
2. Flesh of new cultivar's fruit is red pigmented; parent's flesh is yellow-orange.
3. New cultivar's rind color is a darker orange than that of parent.

4. New variety has red flushed albedo, whereas parent has white albedo.
5. New variety has a thinner, but stronger rind than parent.

COMMERCIAL COMPARISON

The new variety is best compared to the commercial variety, 'Cara-Cara'. 'Red Lina' is similar to 'Cara-Cara' in many horticultural characteristics; however, 'Red Lina' differs in the following;

1. Fruit flesh of 'Red Lina' consistently has a darker red pigment than the red-pink comparator.
2. The rind color of 'Red Lina' is a darker orange than that of Cara-Cara.
3. A high percentage of fruit of 'Red Lina' have red blushed rinds, a characteristic completely absent in Cara-Cara.
4. The new variety has red flushed albedo, whereas comparator has white albedo.

BRIEF DESCRIPTION OF THE PHOTOGRAPHS

The accompanying photographs illustrates in full color examples of typical fruit harvested from 'Red Lina' also known as Rosalina and comparators.

Figure 1:
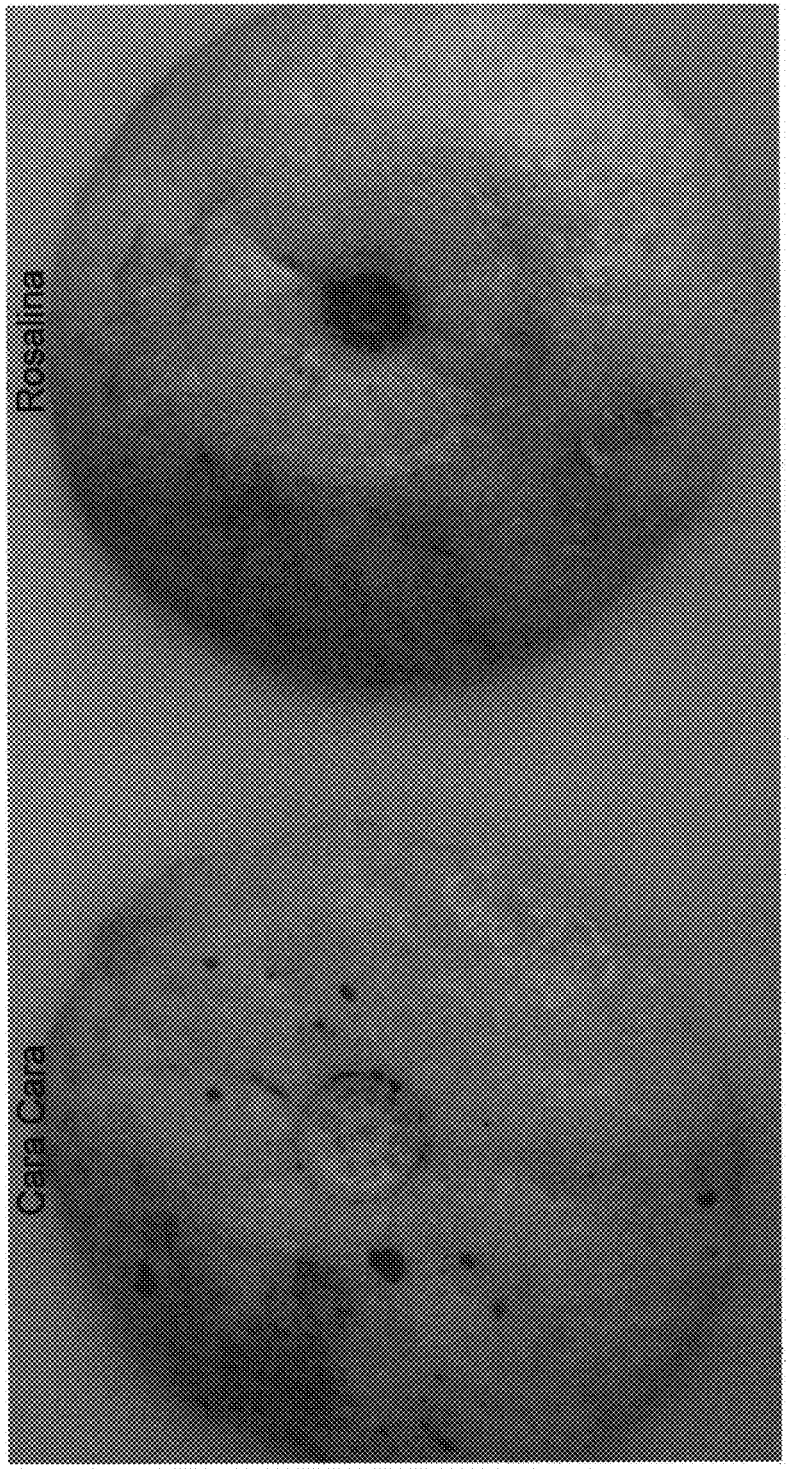
FIG. 1 illustrates a comparison of the calyices 'Red Lina' and 'Cara Cara' on slightly immature fruit.
Figure 2:
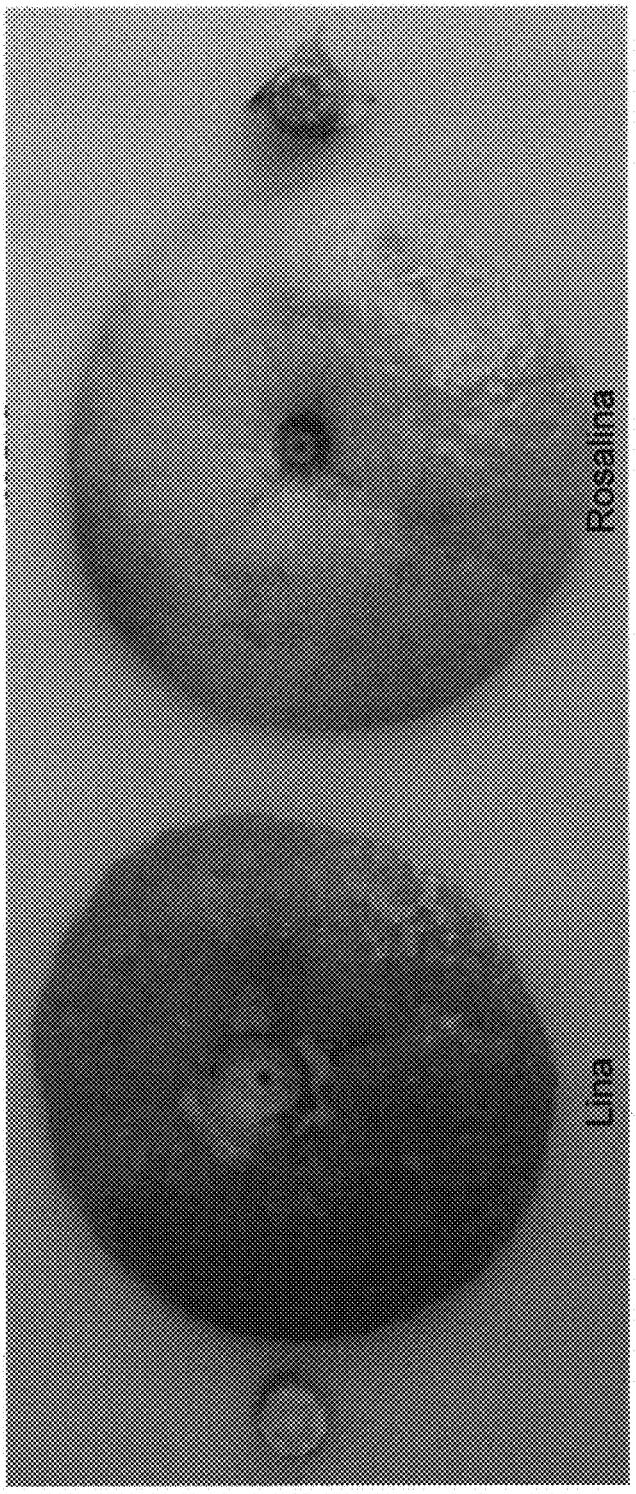
FIG. 2 illustrates a comparison of the calyices 'Red Lina' and 'Lina' on slightly immature fruit.
Figure 3:
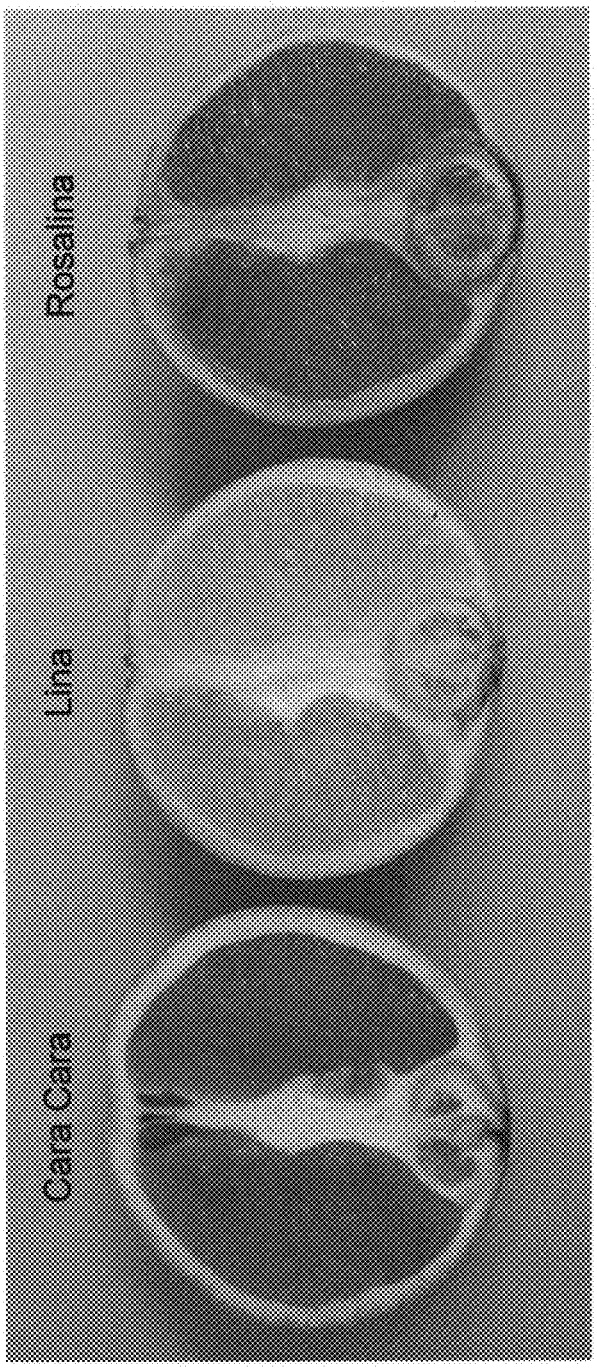
FIG. 3 illustrates a lengthwise comparison of 'Cara Cara', 'Lina' and 'Red Lina'.
Figure 4:
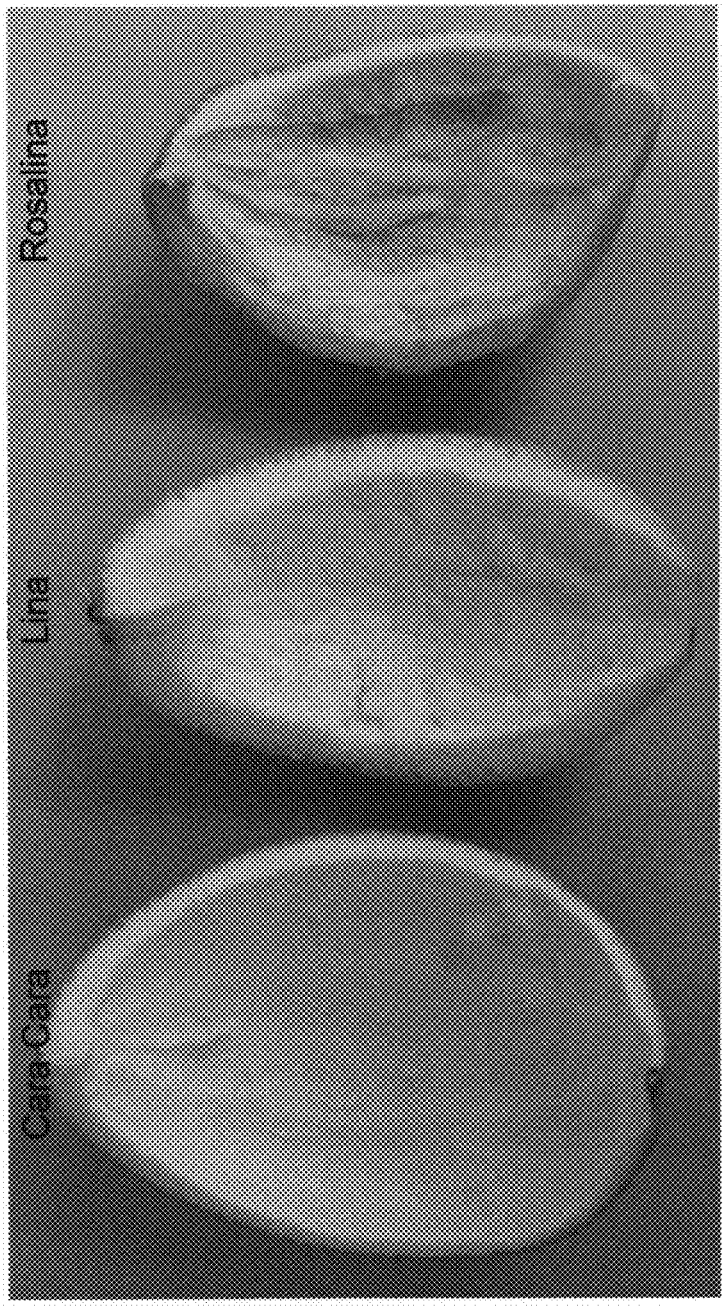
FIG. 4 illustrates albedo of 'Cara Cara', 'Lina' and 'Red Lina'.
Figure 5:
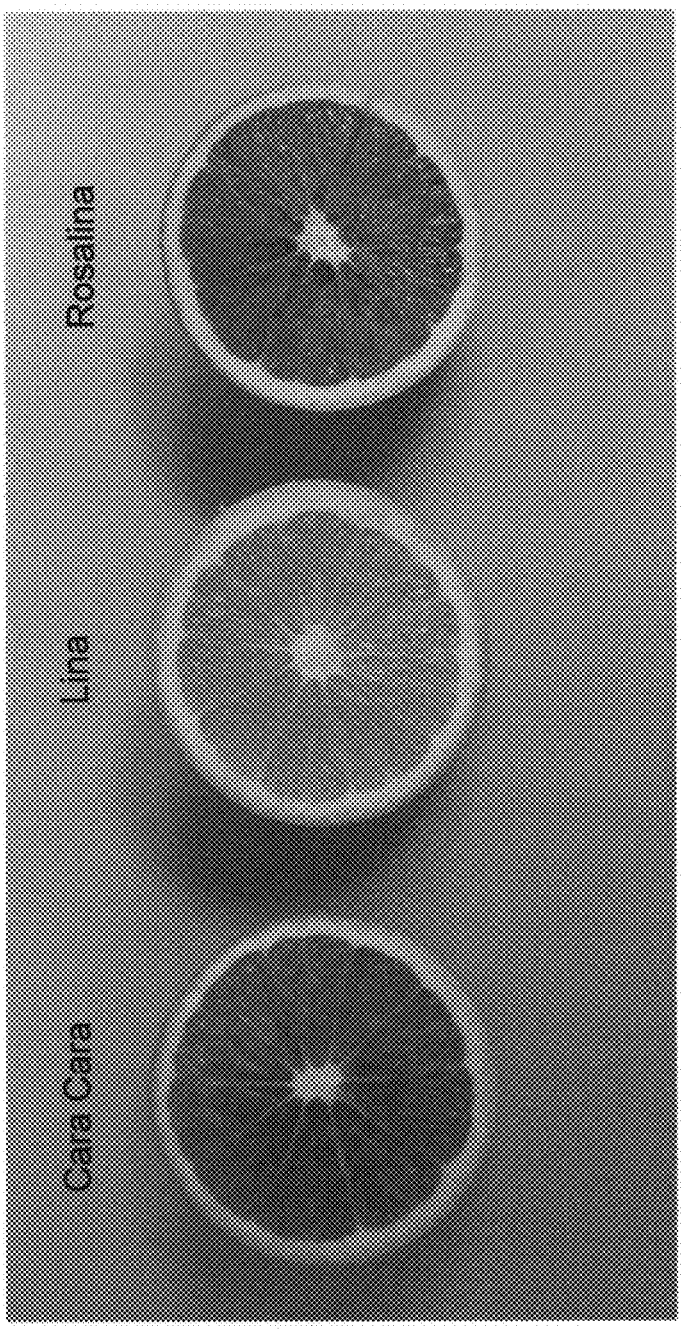
FIG. 5 illustrates a hemispherical cross-section of 'Cara Cara', 'Lina' and 'Red Lina'.
Figure 6:
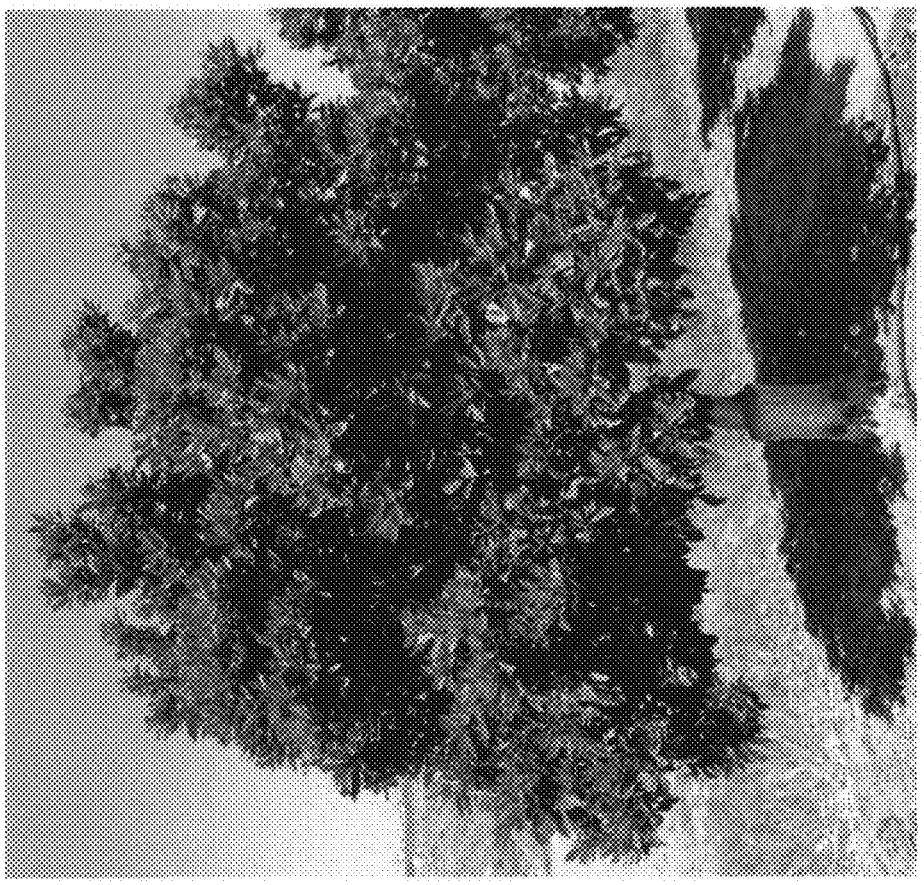
FIG. 6 illustrates a seven-year-old top grafted tree of 'Red Lina' on navel interstock onto Swingle rootstock.
Figure 7:
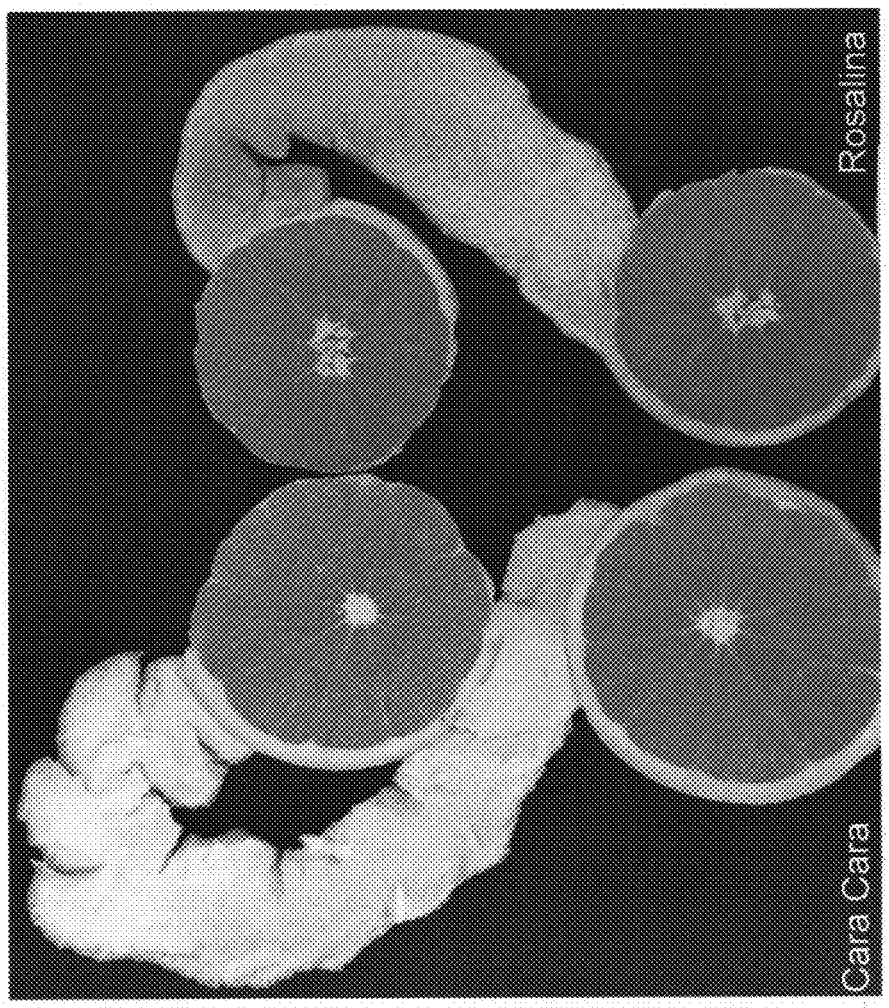
FIG. 7 illustrates 'Red Lina' albedo and flesh color in comparison with the comparator variety Cara-Cara Navel.
Figure 8:
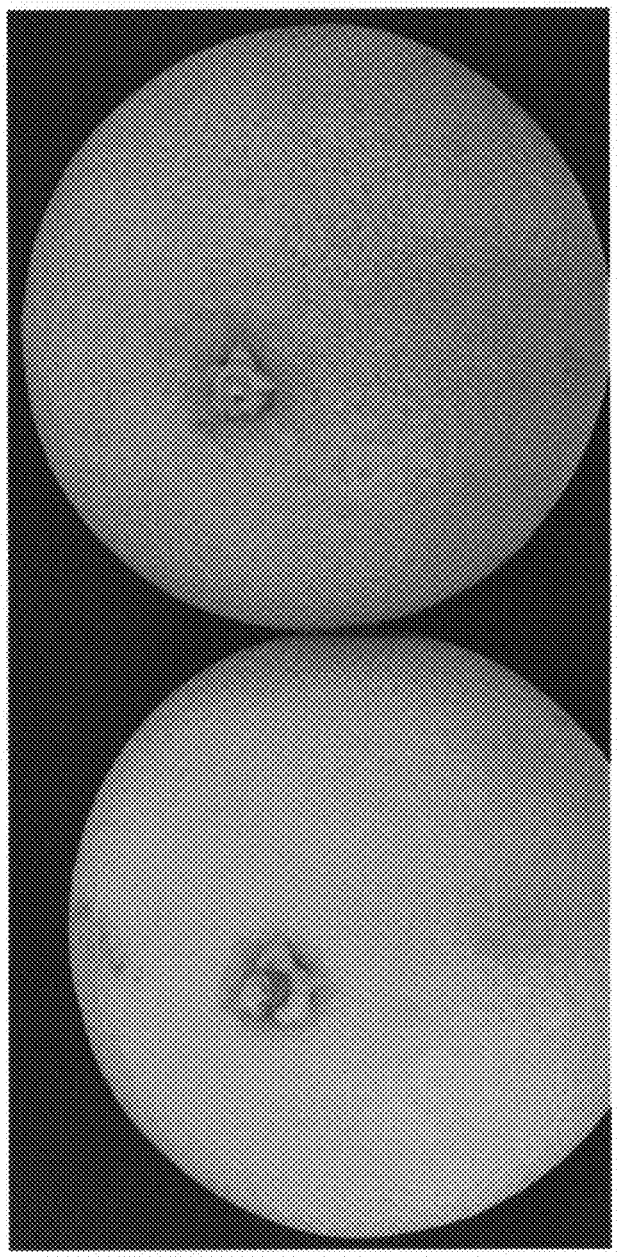
FIG. 8 illustrates 'Red Lina' rind color in comparison with comparator variety 'Cara-Cara'.
Figure 9:
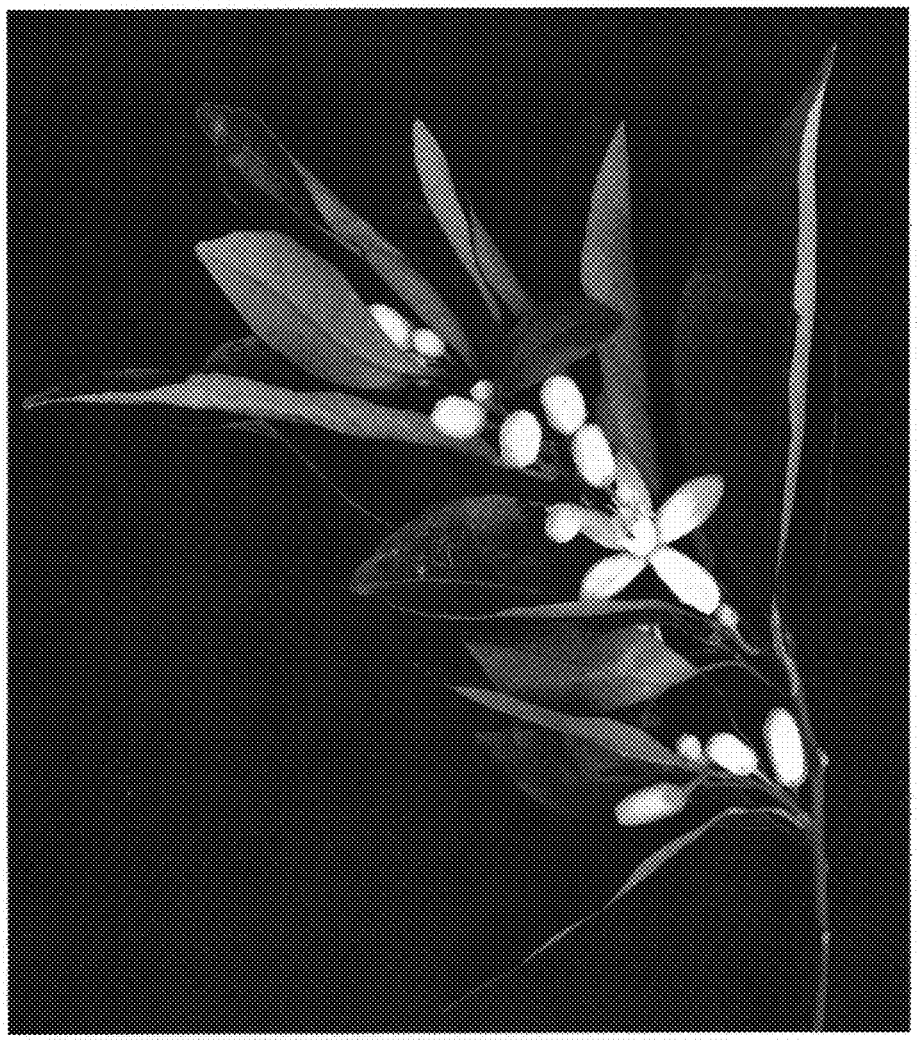
FIG. 9 illustrates flowers and foliage of 'Red Lina'.
Figure 10:
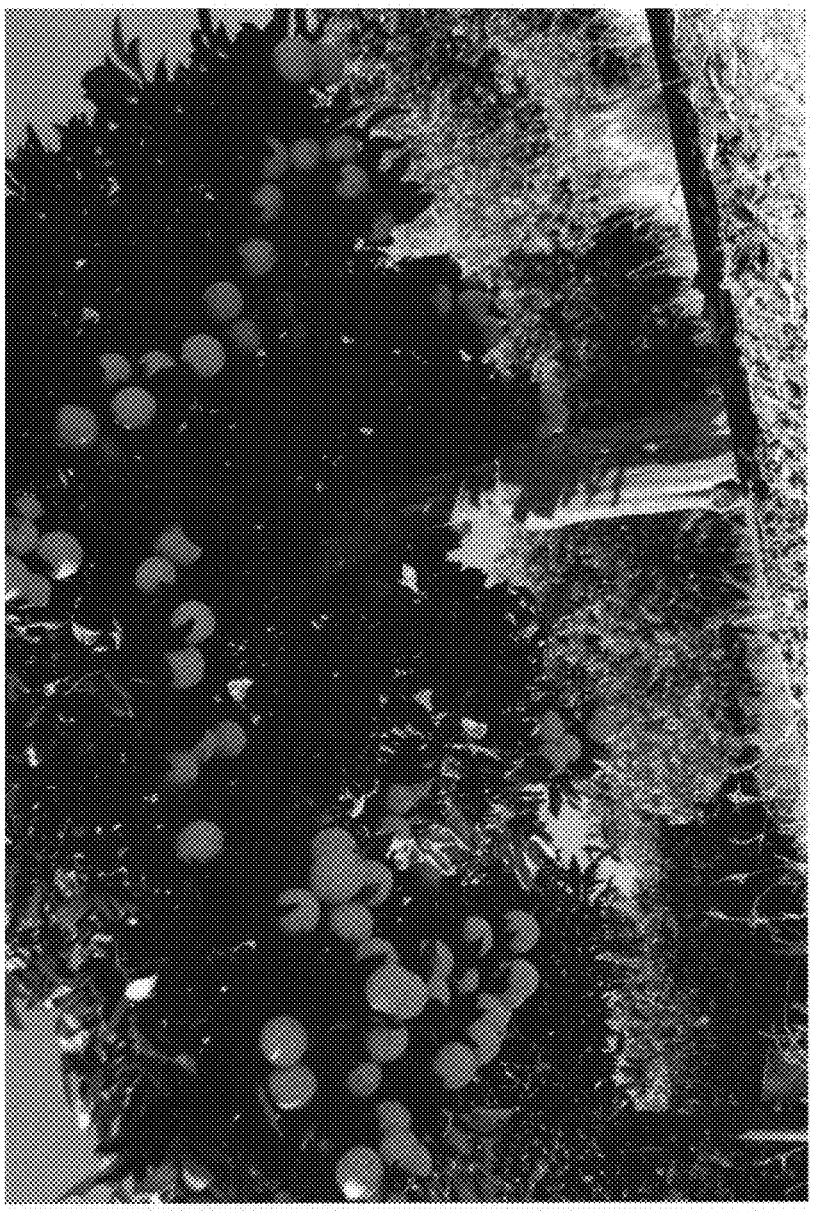
FIG. 10 illustrates a fruiting tree of 'Red Lina' at approximately 7 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Red Lina' plants grown outdoors under commercial trial conditions in the Cape of South Africa. Measurements and numerical values represent an average from the most typical specimens.

Botanical classification: *Citrus sinensis* 'Red Lina'.

PROPAGATION

'Red Lina' is typically grafted onto 'Swingle' rootstock.

PLANT

Age of the plant described: Approximately 7 years.
Plant habit: Upright.
Height: Approximately 2.5 m.
Growth rate: Approximately 3 years to reach 185 cm.
Plant spread: Approximately 2 m.
Length of primary lateral branches: Approximately 52-72 cm.
Quantity of lateral branches: 2-4.
Angle of lateral branches from main trunk: 150-170° degrees.
Branching arrangement: Typically 2-3 more vertical main limbs with 1-2 smaller and more horizontal shoots. The vertical shoots rebranch after 52-72 cm.
Branch diameter: Average 3.8-5.0 cm.
Trunk texture: Minimally rough, slightly striated.
Trunk color: Near RHS Grey-Brown N199A.
Trunk diameter: Average 8.0 cm on a 3 year old plant.
Spines:
*Density*.—Absent.

FOLIAGE

Leaf:
*Average length*.—Range: 6.5-8.25 cm. Average of 7.6 cm.
*Average width*.—Range: 2.8-3.9 cm. Average of 3.2 cm.
*Shape of blade*.—Elliptic.
*Apex*.—Acute.
*Base*.—Broad attenuate.
*Attachment*.—Petiolate.
*Margin*.—Entire to crenate. Absent or weak undulation.
*Texture of top surface*.—Smooth.
*Texture of underside*.—Smooth with raised center rib.
*Aspect*.—Foliage typically upwardly folded. No twisting or blistering with normal cultural conditions.
*Color*.—Mature foliage upper side: Near RHS Green 137A. Mature foliage under side: Near RHS Green 138A.
*Petiole*.—Length: Average length 0.75-1.6 cm. Width: Average 0.3 cm. Pubescence: None. Color: Upper and lower surfaces near Green 143B. Petiole Wing: Approximately 7 mm length. Approximately 2 to 3 mm wide. Color and texture identical to leaf.

FLOWER

Inflorescence and flower type and habit: Single rotate flowers emerging from leaf axils.
Flowering period: Buds form in the Eastern Cape of South Africa in Mid to Late October.
Flower longevity on plant: Approximately 2 weeks.
Persistent or self-cleaning: Self-cleaning.
Bud:
*Shape*.—Ovate.
*Length*.—Average cm.
*Diameter*.—Average 5 mm.
*Color*.—Near RHS White 155A.
Flower size:
*Diameter*.—Average 2.5 cm.
*Depth*.—Average 1.5 cm.
Corolla/petals:
*Arrangement*.—Rotate, fused at base. Not overlapping.
*Petal quantity*.—5.
*Length*.—Average 1.2 cm.
*Width*.—Average 4 to 5 mm.
*Texture*.—Smooth without pubescence.

*Apex*.—Acute.
*Base*.—Fused.
*Margin*.—Smooth.
Color: Petals are RHS White 155D upon abscission.
Calyx/sepals: Filaments separate easily.
*Quantity per flower*.—5.
*Shape*.—Straight.
*Length*.—Average 6-7 mm.
*Width*.—Average 1 mm.
*Texture*.—Smooth.
*Color*.—Upper Surface: Near RHS Green 137A. Lower Surface: Near RHS Green 137A.
Pedicel:
*Length*.—Average 4-5 mm.
*Diameter*.—Average 1 mm.
*Color*.—Near RHS Green 137A.
*Texture*.—Smooth without pubescence.
Fragrance: Sweet, typical *Citrus* flower scent.

REPRODUCTIVE ORGANS

Stamens:
*Number*.—Most commonly 12.
*Filament length*.—Approximately 2.2 cm.
Anthers:
*Shape*.—Globular.
*Length*.—Approximately 0.2 cm.
*Color*.—Near RHS Yellow 3A.
*Pollen*.—Color: Near RHS Yellow 9C. Quantity: Moderate.
Pistil:
*Number*.—1.
*Length*.—Approximately 0.8 cm.
*Style*.—Length: 0.6 cm. Color: Near RHS Green-Yellow 1D.
*Stigma*.—Shape: linear. Color: Near RHS Yellow 8D. Ovary Color: RHS Green 143C.

FRUIT

Color exocarp: Near RHS Orange 26A. About 20 to 30% of fruit exhibits streaks near Red 42C.
Color mesocarp: Near RHS Yellow-Orange 18D, flushed Red 53D.
Flesh color: Near RHS Orange-Red 34B, 34C.
Brix at consumption: 10.4 to 11.6.
Brix at harvest: 12.5. Acid 0.88 Ratio of 10.50.
Diameter: Average diameter at peak: 75 to 85 mm.
Segment number per fruit: Medium, 10 to 11.
General shape: Round.
Fruit neck: Not present.
Stalk end depression: Present, deep.
Stalk end radial grooves: Intermediate quantity of long grooves.
Fruit collar: Absent.
Distal end depression: Absent.
Areola: Absent.
Diameter stylar scar: Large.
Persistence of style: None.
Naval opening: Always present, medium in size. Absent or weak bulging.
Skin/rind texture: Medium to rough. Pitting and pebbling present. Sparse pitting. Peddling moderate, occurring on oil glands only.
Rind: Medium thickness, medium strength.
Oil glands: Small to medium, very little difference in size. Moderate conspicuousness.
Rind oil: Moderate quantity of oil. Inner surface oil glands conspicuous.
Fruit core: Densely filled.
Rudimentary segments: Variable, from weak to intermediate.
Segment wall strength: Moderate.
Fruit juiciness: Moderate.
Juice vesicles: Medium to long: 8 to 12 mm, thin to medium thickness, 1.5 to 2 mm. Low to medium conspicuousness.
Seeds: Not observed to date.
Shipping quality: Excellent storage life observed, better than parent variety. In shelf-life tests and hanging on tree, less waste has been observed, less fallen waste fruit is retrieved compared to parent variety. In a test of over 100 fruit graded, rind creasing is observed at less than 5%, whereas the parent consistently shows 5 to 10%.

OTHER CHARACTERISTICS

Disease/pest resistance: No susceptibility nor resistance observed.
Temperature tolerance: Tolerates low temperatures to approximately −5° C. without negative effects, tolerates high temperatures to approximately 37° C. without negative effects.

What is claimed is:

1. A new and distinct Orange tree named 'Red Lina' as herein illustrated and described.

* * * * *